United States Patent [19]

Platts

[11] Patent Number: 5,403,337

[45] Date of Patent: Apr. 4, 1995

[54] RETRACTABLE-BLADED SURGICAL SCALPEL

[76] Inventor: David Platts, 1932-B 42nd St., Los Alamos, N. Mex. 87544

[21] Appl. No.: 271,047

[22] Filed: Jul. 5, 1994

[51] Int. Cl.⁶ .............................................. A61B 17/32
[52] U.S. Cl. ..................................... 606/167; 30/151; 30/335
[58] Field of Search ............... 606/166, 167, 172, 181, 606/182, 185, 170; 30/2, 151, 162, 164, 167, 286, 335; 128/751

[56] References Cited

U.S. PATENT DOCUMENTS

| | | |
|---|---|---|
| 2,735,176 | 5/1953 | Costin . |
| 3,657,812 | 4/1972 | Lee . |
| 3,905,101 | 9/1975 | Shepherd . |
| 3,906,626 | 9/1975 | Riuli .................................... 30/162 |
| 4,805,304 | 2/1989 | Knoop . |
| 5,071,426 | 12/1991 | Dolgin et al. . |
| 5,201,748 | 4/1993 | Newman et al. . |
| 5,344,424 | 9/1994 | Roberts ............................... 606/167 |

Primary Examiner—Stephen C. Pellegrino
Assistant Examiner—William Lewis
Attorney, Agent, or Firm—Samuel M. Freund

[57] ABSTRACT

A surgical scalpel having a replacable, retractable cutting blade which may be locked in the operating or deployed position using a single digit on one hand is described. Safety of hospital personnel and medical waste disposal personnel is achieved without loss of function or convenience of the scalpel.

6 Claims, 4 Drawing Sheets

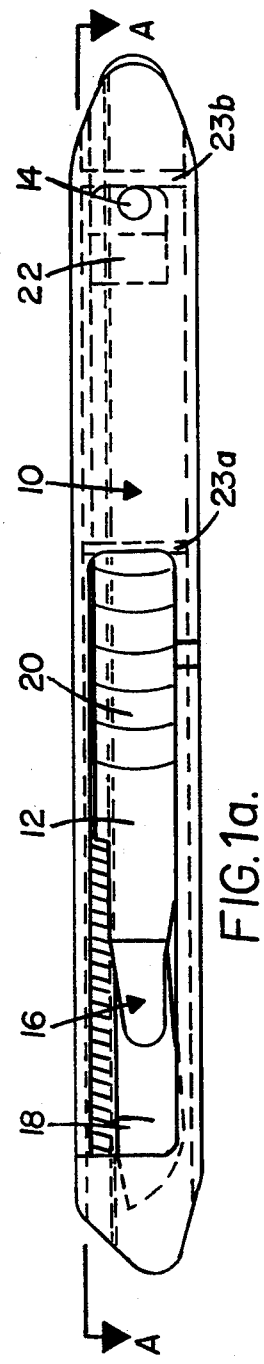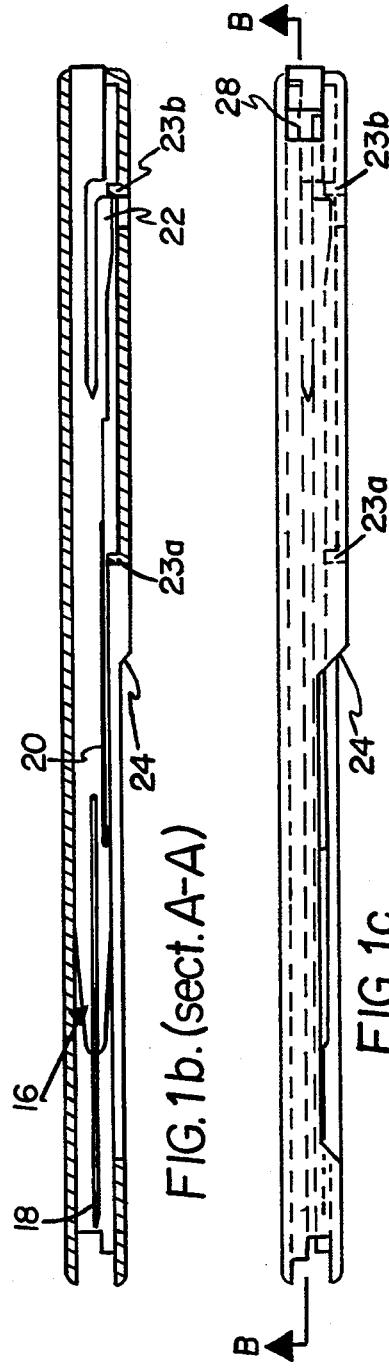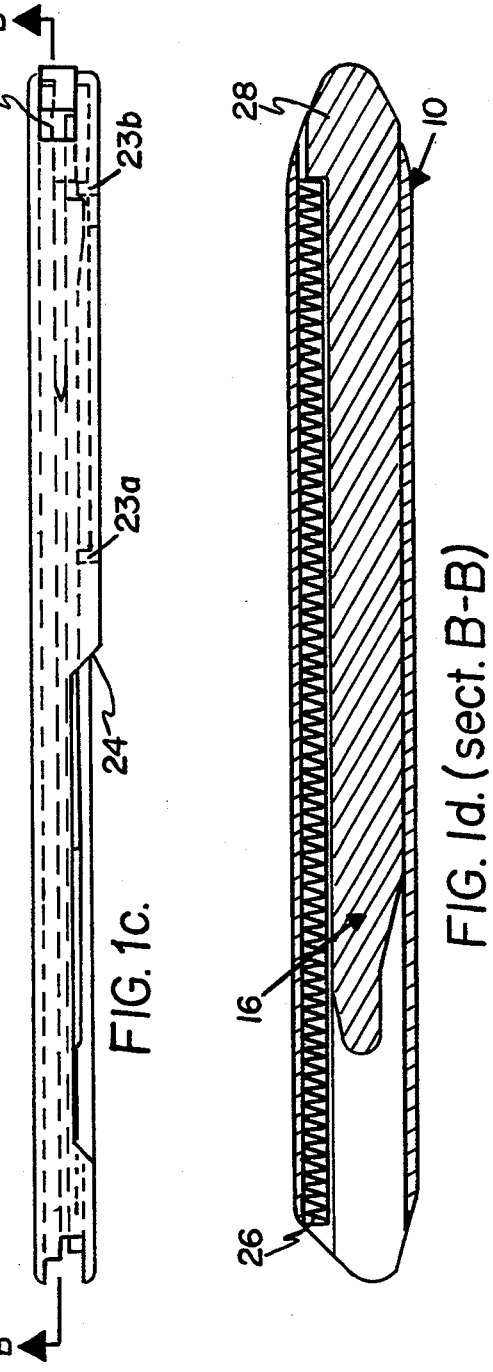

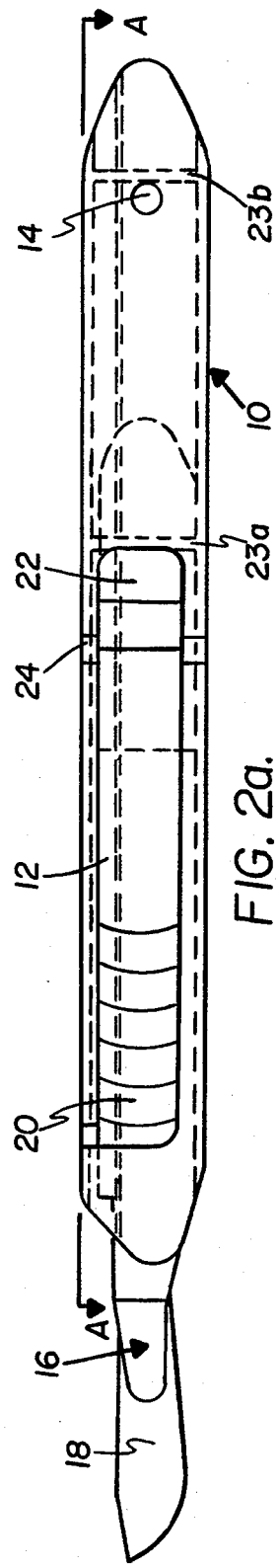
FIG. 2a.
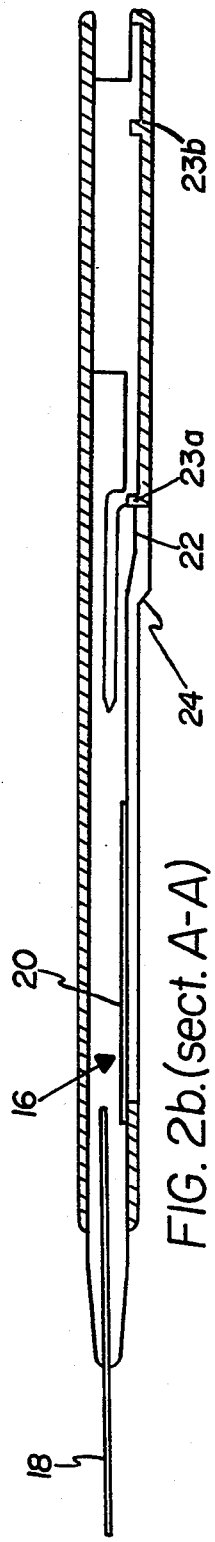
FIG. 2b.(sect. A-A)
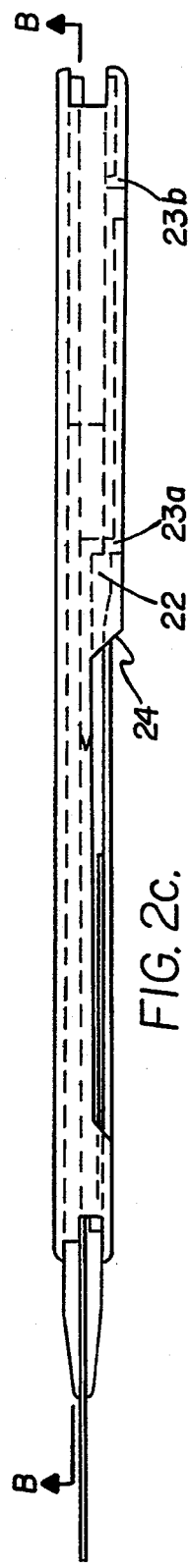
FIG. 2c.
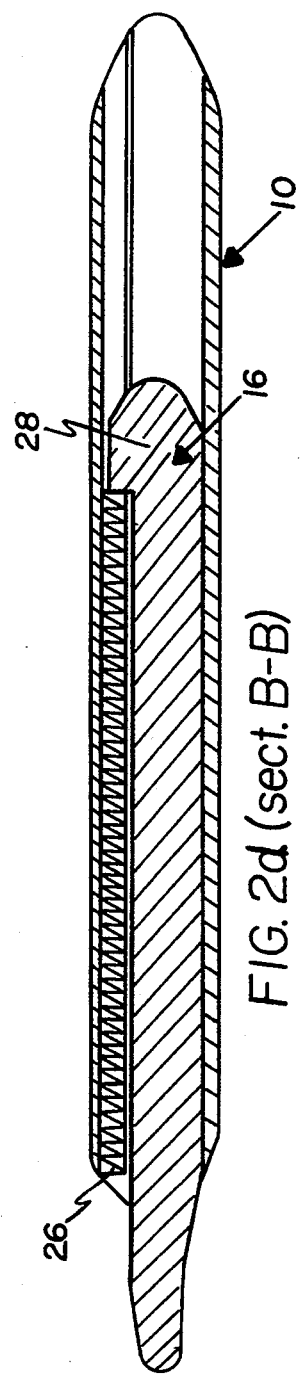
FIG. 2d (sect. B-B)

RETRACTABLE-BLADED SURGICAL SCALPEL

BACKGROUND OF THE INVENTION

The present invention relates generally to surgical cutting instruments, and more particularly to surgical scalpels having retractable blades.

It is well known that existing surgical cutting implements provide a significant potential for harm to surgeons and s up port personnel. That is, with attention directed toward the patient, rapid handling of surgical instruments with exposed sharp edges occasionally leads to cuts and puncture wounds, and more often to loss of integrity of surgical gloves increasing. With increasing risk of life-threatening infectious diseases, it is imperative that such risks be minimized.

Utility knives having retractable blades are well known. For example, U.S. Pat. No. 4,805,304 for "Utility Knife Having A Sliding Blade Holder," which issued to Heinz-Pete Knoop Feb. 21, 1989, describes a knife with a substantially hollow handle having a knife blade guided longitudinally in a knife blade guide track and at least one slider member coupled with the handle side of the longitudinally movable knife blade. The slider member penetrates a wall of the handle in a slider member longitudinal slot the handle broad side. The slot opens at both broad sides. The slider member has on each of the handle broad sides an operating piece engageable by a thumb. Both of the operating pieces receive between themselves and the knife blade at least one guide strip extending parallel to the handle longitudinal axis. The slider member is spring loaded for retraction and requires continuous thumb operation unless a locking device is employed. Thus, if the thumb is removed and a locking device is not employed, the knife blade is automatically pulled back into the knife handle.

Surgical knives have been described wherein various types of blade protection is available. U.S. Pat. No. 3,905,101 for "Disposable Surgical Scalpel," issued to John W. Shepherd on Sep. 16, 1975. Therein is described a single, monassembly, disposable surgical scalpel which includes a handle, a cutting blade attached to the handle, a sheath movably attached to the handle, means for releasably locking the sheath whereby the blade is sheathed, and means for releasably locking the sheath in a position which exposes the blade. Although the sheathable instrument taught by Shepherd would achieve the desired increase in safety for operating room personnel, two hands are required to operate the locking mechanism, thereby rendering the instrument considerably more cumbersome to use than conventional scalpels.

Similarly, for U.S. Pat. No. 2,735,176 for "Veterinary Surgical Knife," which issued to William J. Costin on May 22, 1953. Therein is described a surgical knife which includes a hollow ground blade of surgical steel and a hollow handle into which the blade can be fully retracted for protection while the blade is not in use and from which the edged portion of the blade can be projected for use with the blade disposed substantially in longitudinal alignment with the handle. The locking mechanism taught includes a threaded pin attached to the blade which extends through a slot in the handle, and a knob which is threaded onto the pin for locking the blade in either an extended or withdrawn position. Two hands are required for successful operation of the Costin invention.

U.S. Pat. No. 5,201,748 for "Retractable-Bladed Surgical Scalpel," which issued to Philip H. Newman et al. on Apr. 13, 1993, describes a spring-operated retractable-bladed surgical scalpel. In use, this instrument was found to undesirably and unpredictably propel the slide member thereof carrying the surgical blade out of the rear of the instrument when the operator has inadvertently placed his or her finger in the rear window of the scalpel handle into which the deformable latching mechanism of the scalpel extends when an already-deployed scalpel is to be made safe by causing the blade-carrying slide to retract into the scalpel handle. Moreover, the instrument was found to retract when in its deployed, locked position when the operator's finger is inadvertently placed on the finger-engaging portion of the slide member.

Accordingly, it is an object of the present invention to provide surgical scalpels having retractable blades which may be locked in either a deployed or a retracted position.

Another object of our invention is to provide surgical scalpels having retractable blades which may be locked in either a deployed or a retracted position and which may be operated using one digit of one hand.

Yet another object of the invention is to provide surgical scalpels having retractable blades which may be locked in either a deployed or retracted position, but which cannot accidentally be deployed or retracted.

Still another object of our invention is to provide surgical scalpels having retractable blades for which blades may be changed during a surgical procedure.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the retractable-blade surgical scalpel of this invention includes a generally flat, elongated handle having two generally flat sides, each having an interior flat recessed inner surface which together form an elongated cavity within the handle extending over its long dimension and opening to the outside at the blade end, one side having two windows, the window closest the blade end being elongated along the long dimension of the handle, the other side of the handle having an interior elongated slot which terminates before reaching the blade end of the handle and opening into the cavity toward the slotted side of the handle, the cavity and the interior slot both opening to the outside at the end of the handle away from the blade end, the window side also having a first tab located between the window closest to the blade end of the handle and the second window and extending part way into the elongated cavity, and a second tab located between the second window and the rearward end of said handle and extending part way into the elongated cavity; a surgical cutting blade; a flat, elongated slide member adapted to move horizontally through the cavity in the handle for holding the surgical cutting blade and having a portion adapted to be engaged by and actuated by a single digit of one hand through the elongated window in the side of the handle member, having a raised, deformable latch in the region of the slide member away from the end which holds the blade and on the digit-engaging portion side thereof, and having a tab portion disposed perpendicular to the flat dimension of the slide in a direction away from the digit-engaging portion adapted to slidably move in the interior slot in one side of the handle; and a coil spring located within the interior slot in one side of the handle along the long dimension thereof and adapted to continuously contact the tab portion of the slide, thereby providing a force on the slided directed away from the blade end thereof; whereby the blade may be reversibly locked either entirely within the handle or extend through the opening in the blade end thereof for use in surgical procedures without continuous contact being required with the digit-engaging portion when the slide is moved sufficiently away from the blade end of the handle to permit the raised, deformable latch to engage the second tab which counteracts the action of the coil spring, or when the slide is moved sufficiently toward the blade end of the handle to permit the raised, deformable latch to engage the first tab which counteracts the action of the coil spring, respectively, and whereby the slide may be reversibly removed for replacement with a fresh blade and slide assembly when the raised, deformable latch is depressed through the second window and the slide is moved away from the blade end thereof.

Preferably, the thickness of the side in which the windows are present is chosen such that the deformable latch cannot be accidentally depressed by the operator of said surgical scalpel through the elongated first window.

Benefits and advantages of the present surgical scalpel invention include direct, single digit/single-handed operation, blade stability, either in the extended or retracted positions, and certain, readily-obtainable protection for personnel the operating room and personnel involved in hospital waste disposal since the blade thereof cannot accidentally be deployed.

BRIEF DESCRIPTION OF THE DRAWINGS

The accompanying drawings, which are incorporated in and forms a part of the specification, illustrate an embodiment of the present invention and, together with the description, serve to explain the principles of the invention.

FIG. 1a–d shows a schematic representation of the side, top, and cross sectional views of the assembled scalpel of the present invention, and illustrates the handle, slide and blade thereof in the locked, retracted safety position.

FIGS. 2a–b show a schematic representation of the side, top, and cross sectional views of the assembled scalpel of the of the present invention, and illustrates the hadnle, slide and blade thereof in the locked, cutting (depolyed) position.

DETAILED DESCRIPTION OF THE PREFERRED EMBODIMENTS OF THE INVENTION

Briefly, the present invention includes a surgical scalpel having a retractable blade which may be locked in the operating or deployed position using a single digit on one hand.

Figure 1E:
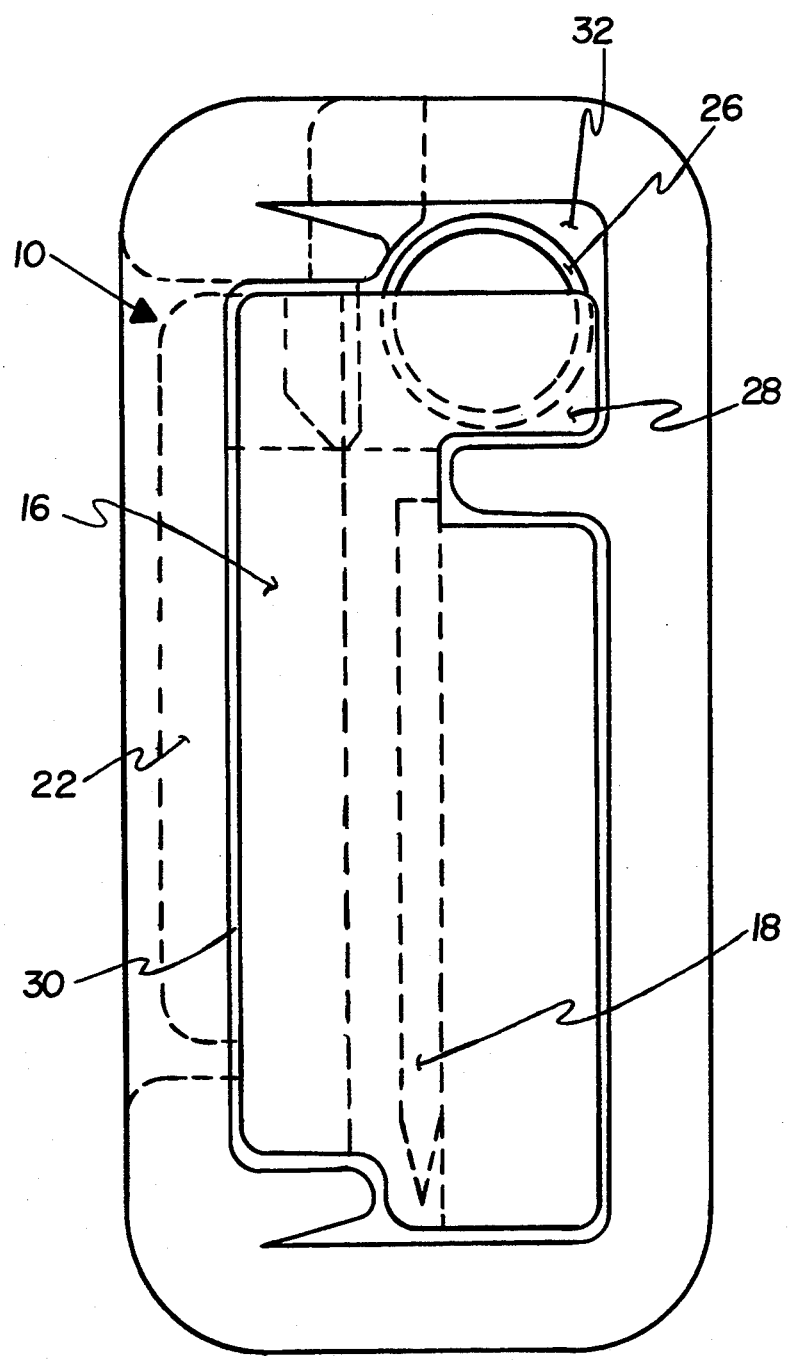
FIG. 1e shows a schematic representation of the rear view of the present invention, and illustrates the handle cavity within which the slide moves, the internal elongated slot in one side of the handle in which the restoring coil spring is located, and the coil spring-engaging tab of the slide.

Reference will now be made in detail to the present preferred embodiments of the invention, an example of which is illustrated in the accompanying drawings. Identical or similar structure is identified by the same callouts. FIG. 1a shows a schematic representation of the side view of the assembled scalpel of the present invention with the surgical blade in its retracted position, while FIG. 1b shows the designated A—A mechanical view thereof. Handle 10 has two windows, 12 and 14, located therein. The forward window 12 is elongated. Slide member 16 is adapted to hold surgical cutting blade 18, and further has a digit-engaging toughened portion 20 adapted to be engaged by a thumb or finger, and a raised, deformable latch member, 22. Tabs 23a and 23b extend into the cavity in handle 10 in which slide member 16 travels and engages deformable latch member 22. The handle is relieved 24 above window 12 in order to render roughened portion 20 more accessible to the operating digit. FIGS. 1c and 1d show a schematic representation of the top view and the designated B—B mechanical view of our scalpel, respectively. Illustrated is coil spring 26 and spring-engaging tab 28 which together transmit a continuous rearward force to slide member 16. Deformable latch member 22 is adapted such that it may engage either front tab 23a or rear tab 23b, while being deformable such that slide member 16 can be slidably moved through the handle cavity under the action of coil spring 26 or a digit in contact with toughened portion 20. Spring 26 forces the latch member against either tab 23aor 23b depending on which tab the latch member is located in front of, when no external force is applied to roughened portion 20 of the slide. FIG. 1 illustrates the latch member engaging the rear tab, 23b, and locking the scalpel in its closed or retracted position. By depressing the deformable latch, by inserting a solid object into rear window 14, the operator may remove the slide member from the handle for replacement of blade 18. By choosing window 14 to have small dimensions, slide 16 is prevented from accidentally exiting handle 10 as a result of the action of one of the fingers of the operator. FIG. 1e is a schematic representation of the rear view of the subject scalpel illustrating, in particular cavity 30 in which slide 16 moves, the interior slot 32, in which coil spring 26 is located, deformable latch member 22, spring-engaging tab 28, and coil spring 26.

Tolerances and materials are selected such that the scalpel is stable in its operating or deployed mode yet is easily retracted. For surgical or other medical uses, materials must conform to Food and Drug Administration standards. For example, scalpels must be ethylene oxide or gamma-ray sterilizable, or autoclavable. It is anticipated that the slide and handle portions of our scalpel will be made from dissimilar materials (metal and plastic, or two different plastics, as examples) chosen additionally for their moldability and for their relative coefficients of expansion and friction such that accurate tolerances can be maintained for operating stability, while maintaining ready relative motion and freedom from binding.

The extended or deployed position of blade 18 is illustrated in FIG. 2 hereof. Identical views to those of FIG. 1 are presented. In order to move slide 16 forward to deploy surgical blade 18, the operator simply engages roughened portion 20 with a thumb or finger and pushes the slide forward. When the blade is fully deployed, the operator releases his or her thumb or finger from the slide and spring 26 drives deformable latch member 22 against tab 23a which then locks the scalpel in its deployed position. Since positive action on the part of the operator is required to deploy blade 18, it cannot be accidentally deployed. In order to retract slide 16 one presses the rearward portion of the slide exposed through window 12, thereby depressing latch member 22 and releasing it from engaging tab 23a. Spring 26 then drives the slide to its retracted position where the deformable latch member rear tab 23b. Handle 10 is relieved on its window side in the vicinity of window 12. The shape of the relieved portion 24 is chosen such that an operator may readily engage toughened portion 20 of slide 16 in order to deploy blade 18, while making it more difficult to depress latch member 22 until it is desired to retract the blade. Therefore, latch 22 cannot easily be accidentally released by the operator during use of the instrument.

Figure 3:
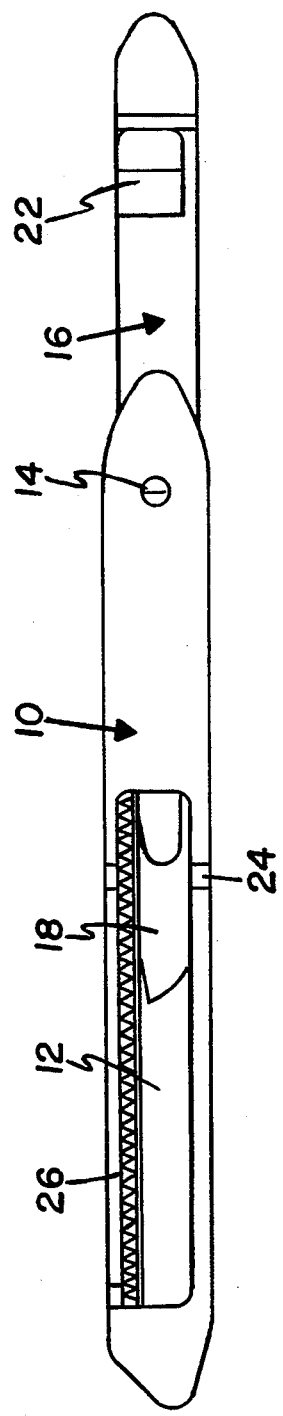
FIG. 3 shows a schematic representation of the present assembled scalpel, and illustrates that the slide/-blade assembly may readily be removed for replacement by depressing the deformable latch through the rear window when the slide is located such that the deformable latch engages the rearmost tab in the handle, and moving the slide out of the handle in the rearward direction.

FIG. 3 illustrates the removal of slide member 16 from handle 10 through the rear opening therein for replacement of surgical blade 18 or of the entire slide member.

The foregoing description of a preferred embodiment of the invention has been presented for purposes of illustration and description. It is not intended to be exhaustive or to limit the invention to the precise form disclosed, and obviously many modifications and variations are possible in light of the above teaching. For example, it would be apparent to one having skill in the surgical arts after carefully studying the present disclosure that the surgical scalpel may be fabricated to accommodate either right- or left-handed operators. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What I claim is:

1. A surgical scalpel having a retractable blade, comprising in combination:
    a. a generally flat, elongated handle member having a forward end and a rearward end, and further having two generally flat sides each having an interior flat recessed inner surface which together form an elongated cavity within said handle member extending substantially over the long dimension thereof and opening to the outside at both the forward end and the rearward end of said handle member, a first side having a first window and a second window spaced-apart from said first window therethrough between the first flat recessed inner surface and the outside of said handle member, the first window being located closer to the forward end of said handle member and being elongated along the long dimension of said handle member, the second side having an interior elongated slot therein which terminates before reaching the forward end of said handle member and opens into the cavity toward the first side, the interior elongated slot opening at the rearward end of said handle member, said first side further comprising a first tab located between the first window and the second window and extending part way into the elongated cavity, and a second tab located between the second window and the rearward end of said handle and extending part way into the elongated cavity;
    b. a surgical cutting blade;
    c. a flat, elongated slide member adapted to slidably move longitudinally through the cavity in said handle member, said slide member further being adapted to receive said surgical cutting blade, having a portion adapted to be engaged by and actuated by a digit through the elongated window in the first side of said handle member, having a raised, deformable latch member in the region of the end of said slide member away from the end thereof which is adapted to receive said surgical cutting blade and on the side thereof having the digit-engaging portion, and having a tab portion disposed in a direction perpendicular to the flat dimension thereof and away from the side thereof having the digit-engaging portion adapted to slidably move in the interior slot in the second side of said handle member; and
    d. coil spring means located within the interior slot in the second side of said handle member disposed generally along the long dimension thereof and adapted to continuously contact the tab portion of said slide member, thereby providing a force on said slide member directed toward the rearward end of said handle member;
    whereby said surgical cutting blade may be reversibly locked either entirely within said handle member or extend outside thereof through the opening therein in the forward end thereof for use in surgical procedures without continuous contact being required with the digit-engaging portion when said slide member is moved sufficiently toward the rearward end of said handle member to permit said raised, deformable latch member to engage said second tab, thereby counteracting the action of said coil spring means, or when said slide member is moved sufficiently toward the forward end of said handle member to permit said raised, deformable latch member to engage said first tab, thereby counteracting the action of said coil spring means, respectively, and whereby said slide member may be removed for replacement when said raised, deformable latch member is depressed through the second window thereby disengaging said second tab, and said slide member is moved away from the forward end thereof.

2. The surgical scalpel having a retractable blade as described in claim 1, wherein said slide member is adapted to removably receive said surgical cutting blade, whereby said surgical cutting blade may be replaced on said slide member.

3. The surgical scalpel having a retractable blade as described in claim 1, wherein the thickness of said first side in the vicinity of the elongated window is chosen such that the operator of said scalpel cannot accidentally depress said raised, deformable latch member of said slide member through the first window when said surgical cutting blade is in its extended and locked position.

4. A surgical scalpel having a retractable blade, comprising in combination:

a. generally flat, elongated handle member having a forward end and a rearward end, and further having two generally flat sides each having an interior flat recessed inner surface which together form an elongated cavity within said handle member extending substantially over the long dimension thereof and opening to the outside at both the forward end and the rearward end of said handle member, a first side having a first window and a second window spaced-apart from said first window therethrough between the first flat recessed inner surface and the outside of said handle member, the first window being located closer to the forward end of said handle member and being elongated along the long dimension of said handle member, the second side having an interior elongated slot therein which terminates before reaching the forward end of said handle member and opens into the cavity toward the first side, the interior elongated slot opening at the rearward end of said handle member, said first side further comprising a first tab located between the first window and the second window and extending part way into the elongated cavity, and a second tab located between the second window and the rearward end of said handle and extending part way into the elongated cavity;

b. a surgical cutting blade;

c. a flat, elongated slide member adapted to slidably move longitudinally through the cavity in said handle member, said slide member further being adapted to receive said surgical cutting blade, having a portion adapted to be engaged by and actuated by a digit through the elongated window in the first side of said handle member, having a raised, deformable latch member in the region of the end of said slide member away from the end thereof which is adapted to receive said surgical cutting blade and on the side thereof having the digit-engaging portion, said latch member being adapted to engage said first tab and said second tab in said handle member, and having a tab portion disposed in a direction perpendicular to the flat dimension thereof and away from the side thereof having the digit-engaging portion adapted to slidably move in the interior slot in the second side of said handle member; and d. coil spring means located within the interior slot in the second side of said handle member disposed generally along the long dimension thereof and adapted to continuously contact the tab portion of said slide member, thereby providing a force on said slide member directed toward the rearward end of said handle member.

5. The surgical scalpel having a retractable blade as described in claim 4, wherein said slide member is adapted to removably receive said surgical cutting blade, whereby said surgical cutting blade may be replaced on said slide member.

6. The surgical scalpel having a retractable blade as described in claim 4, wherein the thickness of said first side in the vicinity of the elongated window is chosen such that the operator of said scalpel cannot accidentally depress said raised, deformable latch member of said slide member through the first window when said surgical cutting blade is in its extended and locked position.

* * * * *